United States Patent
Keyt et al.

(10) Patent No.: US 8,828,388 B2
(45) Date of Patent: Sep. 9, 2014

(54) ANTIBODIES IMMUNOREACTIVE WITH HEREGULIN-COUPLED HER3

(71) Applicant: Trellis Bioscience, LLC, South San Francisco, CA (US)

(72) Inventors: Bruce Keyt, Hillsborough, CA (US); Lawrence M. Kauvar, San Francisco, CA (US); Ellen J. Collarini, Oakland, CA (US); Orit Foord, Foster City, CA (US); Gizette Sperinde, El Granada, CA (US); Marjan Fatholahi, Mountain View, CA (US); Hung Nguyen, American Canyon, CA (US)

(73) Assignee: Trellis Bioscience, LLC, South San Francisco, CA (US)

( * ) Notice: Subject to any disclaimer, the term of this patent is extended or adjusted under 35 U.S.C. 154(b) by 0 days.

(21) Appl. No.: 13/744,299

(22) Filed: Jan. 17, 2013

(65) Prior Publication Data

US 2013/0122000 A1    May 16, 2013

Related U.S. Application Data

(62) Division of application No. 12/770,674, filed on Apr. 29, 2010, now Pat. No. 8,362,215.

(60) Provisional application No. 61/173,670, filed on Apr. 29, 2009.

(51) Int. Cl.
    *A61K 39/395* (2006.01)
    *A61K 39/00* (2006.01)

(52) U.S. Cl.
    USPC ............... 424/138.1; 424/143.1; 424/155.1; 424/181.1; 424/183.1

(58) Field of Classification Search
    None
    See application file for complete search history.

(56) References Cited

U.S. PATENT DOCUMENTS

| | | | |
|---|---|---|---|
| 5,480,968 A | | 1/1996 | Kraus et al. |
| 5,968,511 A | * | 10/1999 | Akita et al. ............. 424/141.1 |
| 6,916,624 B2 | | 7/2005 | Schaefer et al. |
| 7,125,680 B2 | * | 10/2006 | Singer et al. ............. 435/7.2 |
| 2004/0028685 A1 | | 2/2004 | Kinch et al. |
| 2004/0137000 A1 | | 7/2004 | Lynn et al. |
| 2004/0197332 A1 | | 10/2004 | Ullrich et al. |
| 2004/0214272 A1 | | 10/2004 | La Rosa et al. |
| 2007/0027096 A1 | | 2/2007 | Chen et al. |
| 2007/0048315 A1 | | 3/2007 | Presta |
| 2008/0124334 A1 | | 5/2008 | Akita et al. |

FOREIGN PATENT DOCUMENTS

WO   WO-2007/077028   7/2007

OTHER PUBLICATIONS

Cell Signaling product datasheet for phosphor-HER3/ErbB3 (Tyr1289) (21D3) rabbit mAb #4791 (printed May 23, 2012).
Dakappagari et al., J. Biol. Chem. (2005) 280(1):54-63.
International Search Report and Written Opinion mailed Aug. 29, 2010 for International Application No. PCT/US2010/033058, 12 pages.
Menendez et al. J. Clin. Oncol. (2007) 25(17):2496-2498.
Supplementary European Search Report for EP 10770384.5, mailed Dec. 21, 2012.
SWISS-PROT_Q5B3S9, Hypothetical Protein. Oct. 31, 2006. (Retrieved from the Internet on Jul. 22, 2010: <URL: http://www.ncbi.nim.nih.gov/protein/74595631>].
SWISS-PROT_QR2Q0A7, 13S-lipoxygenase. Nov. 28, 2006. [Retrieved from the Internet on Jul. 22, 2010: <URL: http/www.ncbi.nim.nih.gov/protein/122232591>].
Zhou et al., Cancer Cell (2006) 10:39-50.

* cited by examiner

*Primary Examiner* — Laura B Goddard (74) *Attorney, Agent, or Firm* — Morrison & Foerster LLP (57) ABSTRACT

Antibodies which specifically bind heregulin-coupled HER3, at a site distinct from the heregulin binding site, are described. These antibodies are particularly useful in treating cancer.

12 Claims, 7 Drawing Sheets

1G4 mAb can bind and inhibit Her3: heregulin active complex

1G4 Heavy chain VHJ558, DFL16.2, JH1

```
                                                                CDRH1
            G   A   S   V   K   M   S   C   K   A   S   G   Y   T   F   T   D   Y   V   I
  1 CTGGGGCTTC AGTGAAGATG TCCTGCAAGG CTTCTGGATA CACATTCACT GACTATGTTA
    GACCCCGAAG TCACTTCTAC AGGACGTTCC GAAGACCTAT GTGTAAGTGA CTGATACAAT

S   W   V   K   Q   R   T   G   Q   G   L   E   W   I   G   E   I   Y   P   G
 61 TAAGCTGGGT GAAACAGAGA ACTGGACAGG GCCTTGAGTG GATTGGAGAG ATTTATCCTG
    ATTCGACCCA CTTTGTCTCT TGACCTGTCC CGGAACTCAC CTAACCTCTC TAAATAGGAC
            CDRH2
        S   G   R   Y   Y   H   N   E   K   F   K   G   K   A   T   L   T   A   D   K
121 GAAGTGGTAG ATATTACCAC AATGAGAAGT TCAAGGGCAA GGCCACACTG ACTGCAGACA
    CTTCACCATC TATAATGGTG TTACTCTTCA AGTTCCCGTT CCGGTGTGAC TGACGTCTGT
        S   S   N   T   A   Y   I   Q   L   S   S   L   T   S   E   D   S   A   V   Y
181 AATCCTCCAA CACAGCCTAC ATACAACTCA GCAGCCTGAC ATCTGAGGAC TCTGCGGTCT
    TTAGGAGGTT GTGTCGGATG TATGTTGAGT CGTCGGACTG TAGACTCCTG AGACGCCAGA
                                CDRH3
        F   C   T   R   S   L   Q   R   L   R   Y   F   D   V   W   G   A   G   T   T
241 ATTTCTGTAC AAGGTCATTA CAACGGCTAC GGTACTTCGA TGTCTGGGGC GCAGGGACCA
    TAAAGACATG TTCCAGTAAT GTTGCCGATG CCATGAAGCT ACAGACCCCG CGTCCCTGGT
        V   T   V   S   S   A   K   T   T   P   P   S   V   Y   Q   L   S   T
301 CGGTCACCGT CTCCTCAGCC AAAACAACAC CCCCATCTGT CTATCAATTG TCCA
    GCCAGTGGCA GAGGAGTCGG TTTTGTTGTG GGGGTAGACA GATAGTTAAC AGGT
```

1G4 light chain IGKV5-45, JK5 kappa

```
            Q   S   P   A   T   L   S   V   T   P   G   D   R   V   S   L   S   C   R   A
  1 CAGTCTCCAG CCACCCTGTC TGTGACTCCA GGAGATAGAG TCAGTCTTTC CTGCAGGGCC
    GTCAGAGGTC GGTGGGACAG ACACTGAGGT CCTCTATCTC AGTCAGAAAG GACGTCCCGG
                CDRL1
        S   Q   S   I   S   D   Y   L   H   W   Y   Q   Q   K   S   H   E   S   P   R
 61 AGTCAAAGTA TTAGTGACTA CCTTCACTGG TATCAACAGA AATCACATGA GTCTCCAAGG
    TCAGTTTCAT AATCACTGAT GGAAGTGACC ATAGTTGTCT TTAGTGTACT CAGAGGTTCC
                            CDRL2
        L   L   I   K   Y   G   S   Q   S   I   S   G   I   P   S   R   F   S   G   S
121 CTACTCATCA AGTATGGTTC CCAGTCCATC TCTGGGATCC CCTCCAGGTT CAGTGGCAGT
    GATGAGTAGT TCATACCAAG GGTCAGGTAG AGACCCTAGG GGAGGTCCAA GTCACCGTCA
        G   S   G   T   D   F   T   L   S   I   S   S   V   E   T   E   D   F   G   M
181 GGATCACCGA CAGATTTCAC TCTCAGTATC AGCAGTGTGG AGACTGAAGA TTTTGGAATG
    CCTAGTGGCT GTCTAAAGTG AGAGTCATAG TCGTCACACC TCTGACTTCT AAAACCTTAC
                                CDRL3
        Y   F   C   Q   Q   S   N   S   W   P   L   T   F   G   A   G   T   K   L   E
241 TATTTCTGTC AACAGAGTAA CAGCTGGCCT CTCACGTTCG GTGCTGGGAC CAAGCTGGAG
    ATAAAGACAG TTGTCTCATT GTCGACCGGA GAGTGCAAGC CACGACCCTG GTTCGACCTC
                                Mouse kappa
        L   K   R   A   D   A   A   P   T   V   S   A   C   T   R   L   C   P   T   T
301 CTGAAACGGG CTGATGCTGC ACCAACTGTA TCCGCATGCA CCCGACTTTG CCCGACTACG
    GACTTTGCCC GACTACGACG TGGTTGACAT AGGCGTACGT GGGCTGAAAC GGGCTGATGC
```

Figure 7

SEQUENCE LISTING

<160> NUMBER OF SEQ ID NOS: 12

<210> SEQ ID NO 1
<211> LENGTH: 354
<212> TYPE: DNA
<213> ORGANISM: Artificial Sequence
<220> FEATURE:
<223> OTHER INFORMATION: synthetically constructed 1G4 heavy chain
      VHJ558, DFL16.2, JH1
<220> FEATURE:
<221> NAME/KEY: CDS
<222> LOCATION: (3)...(354)

<400> SEQUENCE: 1

```
ct ggg gct tca gtg aag atg tcc tgc aag gct tct gga tac aca ttc          47
   Gly Ala Ser Val Lys Met Ser Cys Lys Ala Ser Gly Tyr Thr Phe
    1               5                  10                  15 act gac tat gtt ata agc tgg gtg aaa cag aga act gga cag ggc ctt         95
Thr Asp Tyr Val Ile Ser Trp Val Lys Gln Arg Thr Gly Gln Gly Leu
                20                  25                  30 gag tgg att gga gag att tat cct gga agt ggt aga tat tac cac aat        143
Glu Trp Ile Gly Glu Ile Tyr Pro Gly Ser Gly Arg Tyr Tyr His Asn
            35                  40                  45 gag aag ttc aag ggc aag gcc aca ctg act gca gac aaa tcc tcc aac        191
Glu Lys Phe Lys Gly Lys Ala Thr Leu Thr Ala Asp Lys Ser Ser Asn
        50                  55                  60 aca gcc tac ata caa ctc agc agc ctg aca tct gag gac tct gcg gtc        239
Thr Ala Tyr Ile Gln Leu Ser Ser Leu Thr Ser Glu Asp Ser Ala Val
    65                  70                  75 tat ttc tgt aca agg tca tta caa cgg cta cgg tac ttc gat gtc tgg        287
Tyr Phe Cys Thr Arg Ser Leu Gln Arg Leu Arg Tyr Phe Asp Val Trp
 80                  85                  90                  95 ggc gca ggg acc acg gtc acc gtc tcc tca gcc aaa aca aca ccc cca        335
Gly Ala Gly Thr Thr Val Thr Val Ser Ser Ala Lys Thr Thr Pro Pro
                100                 105                 110 tct gtc tat caa ttg tcc a                                              354
Ser Val Tyr Gln Leu Ser
            115
```

<210> SEQ ID NO 2

```
<211> LENGTH: 117
<212> TYPE: PRT
<213> ORGANISM: Artificial Sequence
<220> FEATURE:
<223> OTHER INFORMATION: synthetically constructed 1G4 heavy chain
      VHJ558, DFL16.2, JH1 deduced amino acid sequence

<400> SEQUENCE: 2
```

Gly Ala Ser Val Lys Met Ser Cys Lys Ala Ser Gly Tyr Thr Phe Thr
 1               5                  10                  15

Asp Tyr Val Ile Ser Trp Val Lys Gln Arg Thr Gly Gln Gly Leu Glu
             20                  25                  30

Trp Ile Gly Glu Ile Tyr Pro Gly Ser Gly Arg Tyr Tyr His Asn Glu
         35                  40                  45

Lys Phe Lys Gly Lys Ala Thr Leu Thr Ala Asp Lys Ser Ser Asn Thr
 50                  55                  60

Ala Tyr Ile Gln Leu Ser Ser Leu Thr Ser Glu Asp Ser Ala Val Tyr
 65                  70                  75                  80

Phe Cys Thr Arg Ser Leu Gln Arg Leu Arg Tyr Phe Asp Val Trp Gly
                 85                  90                  95

Ala Gly Thr Thr Val Thr Val Ser Ser Ala Lys Thr Thr Pro Pro Ser
            100                 105                 110

Val Tyr Gln Leu Ser
        115

```
<210> SEQ ID NO 3
<211> LENGTH: 354
<212> TYPE: DNA
<213> ORGANISM: Artificial Sequence
<220> FEATURE:
<223> OTHER INFORMATION: synthetically constructed complement of 1G4
      heavy chain VHJ558, DFL16.2, JH1

<400> SEQUENCE: 3
gaccccgaag tcacttctac aggacgttcc gaagacctat gtgtaagtga ctgatacaat      60
attcgaccca ctttgtctct tgacctgtcc cggaactcac ctaacctctc taaataggac    120
cttcaccatc tataatggtg ttactcttca agttcccgtt ccggtgtgac tgacgtctgt    180
ttaggaggtt gtgtcggatg tatgttgagt cgtcggactg tagactcctg agacgccaga    240
taaagacatg ttccagtaat gttgccgatg ccatgaagct acagacccccg cgtccctggt   300 gccagtggca gaggagtcgg ttttgttgtg ggggtagaca gatagttaac aggt          354

<210> SEQ ID NO 4
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: CDRH1 of 1G4 heavy chain VHJ558, DFL16.2, JH1

<400> SEQUENCE: 4
```

Gly Tyr Thr Phe Thr Asp Tyr Val Ser
 1               5

```
<210> SEQ ID NO 5
<211> LENGTH: 7
<212> TYPE: PRT
<213> ORGANISM: Artificial Sequence
<220> FEATURE:
```

```
<223> OTHER INFORMATION: synthetic construct
<220> FEATURE:
<221> NAME/KEY: PEPTIDE
<222> LOCATION: (1)...(7)
<223> OTHER INFORMATION: CDRH2 of 1G4 heavy chain VHJ558, DFL16.2, JH1

<400> SEQUENCE: 5

Ile Tyr Pro Ser Gly Arg Tyr
 1               5

<210> SEQ ID NO 6
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(12)
<223> OTHER INFORMATION: CDRH3 of 1G4 heavy chain VHJ558, DFL16.2, JH1

<400> SEQUENCE: 6

Thr Arg Ser Leu Gln Arg Leu Arg Tyr Phe Asp Val
 1               5                  10

<210> SEQ ID NO 7
<211> LENGTH: 360
<212> TYPE: DNA
<213> ORGANISM: Artificial Sequence
<220> FEATURE:
<223> OTHER INFORMATION: synthetically constructed 1G4 light chain
      IGKV5-45, JK5 kappa
<220> FEATURE:
<221> NAME/KEY: CDS
<222> LOCATION: (1)...(360)

<400> SEQUENCE: 7 cag tct cca gcc acc ctg tct gtg act cca gga gat aga gtc agt ctt       48
Gln Ser Pro Ala Thr Leu Ser Val Thr Pro Gly Asp Arg Val Ser Leu
 1               5                  10                  15 tcc tgc agg gcc agt caa agt att agt gac tac ctt cac tgg tat caa       96
Ser Cys Arg Ala Ser Gln Ser Ile Ser Asp Tyr Leu His Trp Tyr Gln
             20                  25                  30 cag aaa tca cat gag tct cca agg cta ctc atc aag tat ggt tcc cag      144
Gln Lys Ser His Glu Ser Pro Arg Leu Leu Ile Lys Tyr Gly Ser Gln
         35                  40                  45 tcc atc tct ggg atc ccc tcc agg ttc agt ggc agt gga tca ggg aca      192
Ser Ile Ser Gly Ile Pro Ser Arg Phe Ser Gly Ser Gly Ser Gly Thr
     50                  55                  60 gat ttc act ctc agt atc agc agt gtg gag act gaa gat ttt gga atg      240
Asp Phe Thr Leu Ser Ile Ser Ser Val Glu Thr Glu Asp Phe Gly Met
 65                  70                  75                  80 tat ttc tgt caa cag agt aac agc tgg cct ctc acg ttc ggt gct ggg      288
Tyr Phe Cys Gln Gln Ser Asn Ser Trp Pro Leu Thr Phe Gly Ala Gly
                 85                  90                  95 acc aag ctg gag ctg aaa cgg gct gat gct gca cca act gta tcc gca      336
Thr Lys Leu Glu Leu Lys Arg Ala Asp Ala Ala Pro Thr Val Ser Ala
            100                 105                 110 tgc acc cga ctt tgc ccg act acg                                      360
Cys Thr Arg Leu Cys Pro Thr Thr
        115                 120

<210> SEQ ID NO 8
<211> LENGTH: 120
<212> TYPE: PRT
<213> ORGANISM: Artificial Sequence
```

```
<220> FEATURE:
<223> OTHER INFORMATION: synthetically constructed 1G4 light chain
      IGKV5-45, JK5 kappa deduced amino acid sequence

<400> SEQUENCE: 8

Gln Ser Pro Ala Thr Leu Ser Val Thr Pro Gly Asp Arg Val Ser Leu
1               5                   10                  15

Ser Cys Arg Ala Ser Gln Ser Ile Ser Asp Tyr Leu His Trp Tyr Gln
            20                  25                  30

Gln Lys Ser His Glu Ser Pro Arg Leu Leu Ile Lys Tyr Gly Ser Gln
        35                  40                  45

Ser Ile Ser Gly Ile Pro Ser Arg Phe Ser Gly Ser Gly Ser Gly Thr
    50                  55                  60

Asp Phe Thr Leu Ser Ile Ser Ser Val Glu Thr Glu Asp Phe Gly Met
65                  70                  75                  80

Tyr Phe Cys Gln Gln Ser Asn Ser Trp Pro Leu Thr Phe Gly Ala Gly
                85                  90                  95

Thr Lys Leu Glu Leu Lys Arg Ala Asp Ala Ala Pro Thr Val Ser Ala
            100                 105                 110

Cys Thr Arg Leu Cys Pro Thr Thr
            115                 120

<210> SEQ ID NO 9
<211> LENGTH: 360
<212> TYPE: DNA
<213> ORGANISM: Artificial Sequence
<220> FEATURE:
<223> OTHER INFORMATION: synthetically constructed complement of 1G4
      light chain IGKV5-45, JK5 kappa

<400> SEQUENCE: 9
gtcagaggtc ggtgggacag acactgaggt cctctatctc agtcagaaag gacgtccgg       60 tcagtttcat aatcactgat ggaagtgacc atagttgtct ttagtgtact cagaggttcc    120
gatgagtagt tcataccaag ggtcaggtag agacccctagg ggaggtccaa gtcaccgtca   180
cctagtccct gtctaaagtg agagtcatag tcgtcacacc tctgacttct aaaaccttac    240
ataaagacag ttgtctcatt gtcgaccgga gagtgcaagc cacgaccctg gttcgacctc    300
gactttgccc gactacgacg tggttgacat aggcgtacgt gggctgaaac gggctgatgc    360

<210> SEQ ID NO 10
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(11)
<223> OTHER INFORMATION: CDRL1 of 1G4 light chain IGKV5-45, JK5 kappa

<400> SEQUENCE: 10

Arg Ala Ser Gln Ser Ile Ser Asp Tyr Leu His
1               5                   10

<210> SEQ ID NO 11
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
```

```
<222> LOCATION: (1)...(7)
<223> OTHER INFORMATION: CDRL2 of 1G4 light chain IGKV5-45, JK5 kappa

<400> SEQUENCE: 11

Tyr Gly Ser Gln Ser Ile Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)...(9)
<223> OTHER INFORMATION: CDRL3 of 1G4 light chain IGKV5-45, JK5 kappa

<400> SEQUENCE: 12

Gln Gln Ser Asn Ser Trp Pro Leu Thr
 1               5
```

ANTIBODIES IMMUNOREACTIVE WITH HEREGULIN-COUPLED HER3

CROSS-REFERENCE TO RELATED APPLICATIONS

This application is a divisional of U.S. Ser. No. 12/770,674, filed 29 Apr. 2010, now allowed, which claims priority from U.S. provisional application 61/173,670, filed 29 Apr. 2009. The contents of this document are incorporated herein by reference.

REFERENCE TO SUBMISSION OF SEQUENCE LISTING ON ASCII TEXT FILE

The content of the following submission on ASCII text file is incorporated herein by reference in its entirety: a computer readable form (CRF) of the Sequence Listing (file name: 388512012210CorrectedSeqList.txt, date recorded: Jul. 7, 2014, size: 9,147 bytes).

TECHNICAL FIELD

The invention relates to monoclonal antibodies with superior therapeutic value. The antibodies of the invention are particularly selective for cancer cells, and more particularly for cancer cells that secrete certain autocrine growth factors.

BACKGROUND ART

A family of receptors that mediate signaling through tyrosine kinases includes a subfamily of at least four members: HER1 also designated epidermal growth factor receptor (EGFR) is encoded by the ErbB1 gene; HER2 or HER2/neu encoded by the ErbB2 gene, HER3, encoded by the ErbB3 gene and HER4, encoded by ErbB4. Each of these receptors has a multiplicity of synonyms and in the present application, the "HER" terminology and ErbB terminology will be used interchangeably for all the factors, whether discussing protein or nucleic acids.

Figure 1A:
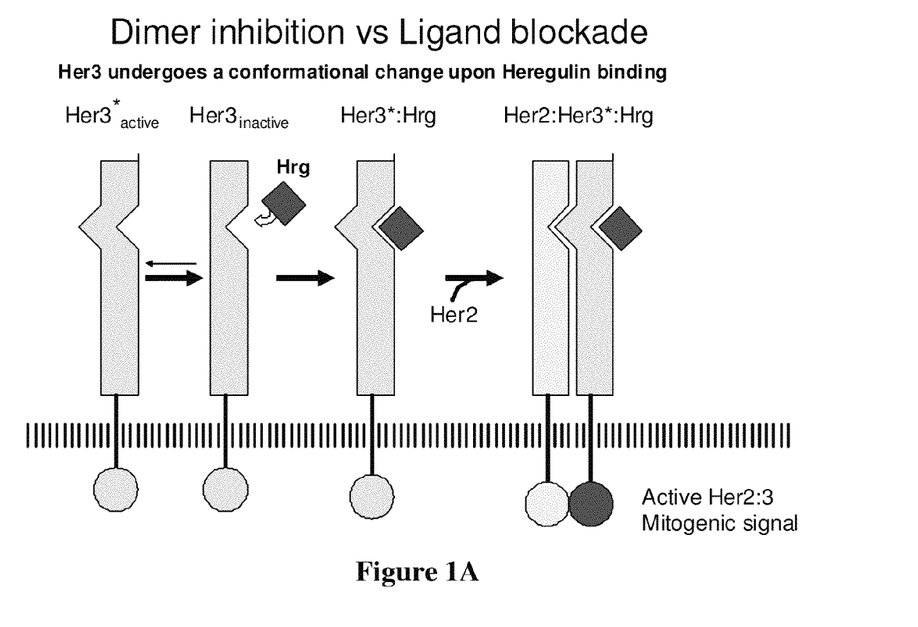
FIGS. 1A and 1B are diagrams of the interaction of HER2 and HER3 in the presence of heregulin (FIG. 1A) and in the presence of both heregulin and either antibody 14B10 or antibody 1G4 (FIG. 1B).

The primary natural ligand for the receptor encoded by ErbB3 is heregulin (HRG), a polypeptide that, when bound to HER3 induces a conformational change that promotes dimerization of HER3 with HER2 through the extracellular domains of each activating the signaling cascade, as shown in FIG. 1A. A similar dimerization is stimulated by the ligand for the HER1 receptor, Epidermal Growth Factor (EGF), which also activates a signaling cascade intracellularly.

Antibodies, including monoclonal antibodies to HER3 have been prepared. U.S. Pat. No. 5,480,968 discloses antibodies that bind specifically to ErbB3 and do not bind to ErbB2 or ErbB1. U.S. Pat. No. 5,968,511 discloses and claims antibodies that bind to HER3 and reduce heregulin-induced formation of an HER2-HER3 protein complex in cells that express both of these receptors or which antibodies increase the binding affinity of heregulin for ErbB3 protein or which reduce activation of the downstream signaling. Although only murine antibodies are prepared, humanized antibodies are also claimed.

Published U.S. application 2004/0197332 describes and claims anti-HER3 antibodies that downregulate the expression of HER3. PCT Publication WO2007/077028 describes antibodies that bind to HER3 that are produced in XenoMouse® and are thus fully human by sequence. Most of these antibodies are described as binding to the major ligand binding domain (L2) of the extracellular domain of HER3, but the binding is destroyed if the three-dimensional structure of the extracellular domain is disrupted. Further, the antibodies described in this publication compete with HRG for binding to HER3.

DISCLOSURE OF THE INVENTION

It has now been found possible to obtain antibodies that bind at a much higher affinity to HER3 when it is complexed with heregulin than to uncomplexed HER3. Such antibodies are particularly valuable since they are most effective in the context of tumor cells that secrete heregulin or analogous agonist peptides, thus stimulating the signaling cascade at a higher level than in normal cells. This enhances the specificity of the treatment to those tumor cells that are most aggressive in their invasive growth properties, while minimizing toxicity to normal cells that are not being intensively stimulated. Further, the novel antibodies are effective at blocking signaling in cells that over-express HER1 and HER3, providing a desirable "pan-HER" activity (Huang, Z, et al., *Expert Opin Biol Ther.* (2009) 9:97-110).

MODES OF CARRYING OUT THE INVENTION

The present invention provides monoclonal antibodies with unique specificities for the heregulin-bound active form of HER3, thus, preferentially inhibiting dimerization and downstream signaling in environments with high concentrations of heregulin. Such high concentrations characterize many tumor cells. By targeting cells bathed in a high local concentration of stimulatory ligand, toxicities arising from blocking signaling from lower concentrations in normal cells can be minimized (Bria, E, et al., *Expert Opin Biol Ther.* (2008) 8:1963-1971).

The use of antibodies that preferentially bind a HER3: heregulin complex is advantageous since they are most effective on cells, such as cancer cells that are dependent on the complex signaling for growth. This type of cell is characteristic of many tumors.

Thus, the invention is directed to monoclonal antibodies and pharmaceutical compositions thereof wherein these antibodies bind to heregulin activated HER3 with an affinity at least five times their affinity for HER3 not bound to heregulin, preferably ten times greater, at all values between 5 and 10, and at values greater than 10. Preferably, the affinity of the antibody will be at least that represented by a kD of 5 nM for HER3 itself, more preferably that represented by a kD of at least 2 nM and more preferably that represented by a kD of 100 pmol.

The monoclonal antibodies may take many forms, including chimeric forms wherein the variable regions are of one species and the constant regions of another; forms consisting only of the variable regions, single-chain forms; and the like. Thus, "antibodies" refers both to whole antibodies and to fragments thereof that exhibit the required immunospecificity. In some cases, this is spelled out, but if not, fragments are intended to be included in this term unless it is otherwise obvious from context.

The antibodies of the invention can be obtained by extensive screening of hybridomas or immortalized cells of laboratory animals such as rats, mice and rabbits immunized with appropriate immunogens. Appropriate immunogens include those exemplified below, as well as portions of the HER3 protein that have been treated with heregulin. The antibodies thus produced are screened for their ability to bind heregulin-bound HER3 differentially from HER3 itself. These antibodies can then be humanized using procedures now commercially available to obtain antibodies suitable for administration to humans.

In one particular example set forth below, an antibody with this desirable differential binding affinity, 1G4, was prepared. Humanized forms and human analogs of this antibody are included within the scope of this invention.

The hybridoma that produces IG4 was deposited with the American Type Culture Collection, 10801 University Boulevard, Manassas, Va. 20110, under the terms of the Budapest Treaty on 29 Apr. 2010. Upon issuance of a U.S. patent disclosing this hybridoma, all restrictions on this deposit will be irrevocably removed.

Figure 7:
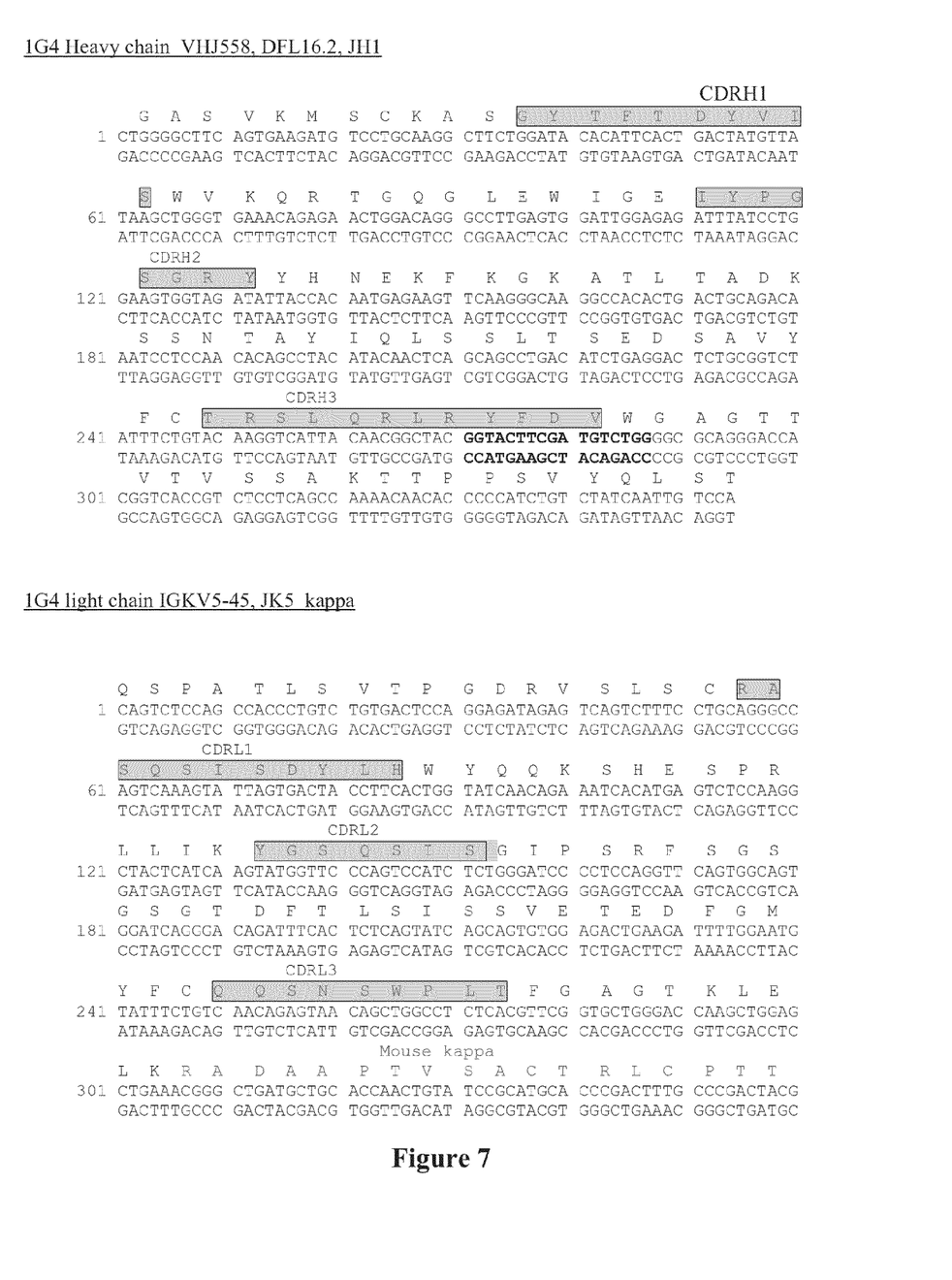
FIG. 7 (SEQ ID NOS:1-12) shows the nucleotide sequence encoding 1G4 heavy chain (SEQ ID NO:1) and 1G4 light chain (SEQ ID NO:7) and deduced amino acid sequences (SEQ ID NO:2 and SEQ ID NO:8).

In addition, FIG. 7 shows the nucleotide sequence and amino acid sequences of the heavy chain and light chain of 1G4 respectively. The CDR of the heavy chain are: CDRH1: GYTFTDYVS (SEQ ID NO:4); CDRH2:IYPSGRY (SEQ ID NO:5); CDRH3:TRSLQRLRYFDV (SEQ ID NO:6). The CDR of the light chain are CDRL1:RASQSISDYLH (SEQ ID NO:10); CDRL2:YGSQSIS (SEQ ID NO:11); CDRL3: QQSNSWPLT (SEQ ID NO:12).

Alternatively, laboratory animals that produce human antibodies directly can be used as subjects to produce antibodies that are human. Thus, the immunogen can be administered to animals such as the XenoMouse® that will provide directly the human antibodies desired. These antibodies are screened in a manner similar to that employed in screening hybridomas or other immortalized rodent cells.

Typical procedures simply compare the measured affinity of the various antibodies in the screen with respect to HER3 and HER3 coupled to heregulin. A variety of assays is appropriate for this, and straightforward commercially available assays include those marketed as Biacore™ and FortéBio®.

Preferably, however, the proprietary technology Cell-Spot™ described in U.S. Pat. No. 7,413,868 incorporated herein by reference may be used. This permits millions of hybridomas and splenocytes or lymphocytes to be screened in practical time frames.

Suitable antibodies can also be obtained directly from human beings, since individuals harboring tumors, for example, that produce heregulin:HER3 complexes will generate antibodies to these tumor antigens. In general, antibodies immunospecific for tumor antigens are produced by such subjects. See, for example, Pavoni, E., et al., *BMC Biotechnology* (2007) 770:1-17. In addition, patients with autoimmune diseases such as lupus make antibodies to cell antigens not necessarily associated with tumors. Because of the large number of cells that can be sampled, even very rare antibodies can be obtained in this fashion.

When suitable cells secreting the desired antibodies have been identified in the screen, the antibodies can then be produced recombinantly using well known techniques. The nucleotide sequences encoding the antibodies are obtained from cells secreting them and suitable expression constructs prepared to transfect host cells for such recombinant production. The ability to produce such antibodies recombinantly permits variants such as single chain antibodies to be produced. A variety of cells can be used for such production including insect, mammalian and plant cells, as well as microorganism cultures.

The antibodies of the invention, and fragments thereof, in particular, human and humanized forms of them, are useful in treating cancers that are associated with heregulin-stimulated signaling. These include cancers of the breast, uterus, ovary, prostate, kidney, lung, pancreas, stomach, salivary gland, colon, colon-rectal, thyroid, bladder, skin, or any cancer exhibiting heregulin-stimulated proliferation. It may be useful to evaluate the cancer to be treated for its ability to secrete heregulin in connection with conducting treatment using the antibodies of the invention. This may be done by culturing cells from a biopsied cancer sample or by in situ testing of the tumor in vivo. In one method, this is done by contacting said tumor or biopsy thereof with the antibodies or fragments of the invention and determining the level of complex formed as compared to any complex formed with antibodies that bind to uncoupled HER3.

The subjects may be human or veterinary, including, domestic animals such as dogs and cats, farm animals such as pigs, cows and sheep; and laboratory model animals such as rats, mice and rabbits. Laboratory model animals may be particularly useful in evaluating the effect of the antibodies of the invention in the corresponding human tumors, and such use is included within the invention.

For use in treatment, the antibodies of the invention may also be coupled to cytotoxic agents and/or to anti-tumor drugs in general. Such drugs include, for example, platinum-based drugs, cell cycle inhibitors, natural products such as vincristine and various camptothecins.

For administration, the antibodies are formulated according to standard procedures for pharmaceutical compositions of antibodies such as those described in *Remington's Pharmaceutical Sciences,* Mack Publishing Company, Easton Pa., latest edition. These formulations may include delivery vehicles such as liposomes or micelles or may contain standard excipients, such as saline or saccharides.

Typically, the antibody compositions are administered by injection, in particular intravenous injection. However, any mode of administration that is workable with such compositions is included within the scope of the invention.

The production of the antibodies on a practical scale may include standard recombinant methods wherein the nucleotide sequences encoding the antibodies or portions thereof have been isolated and manipulated in standard procedures to obtain the active antibody compositions. Such production is typically in mammalian cell culture, insect cell culture or plant cell culture or may be by plants per se. The antibodies of the claimed characteristics are included within the scope of the inventions regardless of means of production.

The following examples are intended to illustrate but not to limit the invention.

Example 1

Production of 1G4 and Binding Assay

Seven murine hybridoma libraries were prepared by immunizing mice with 293 cells overexpressing HER3 extracellular domain (ECD) along with a polypeptide which consists essentially of the L2 domain of HER3 that had been produced in *E. coli,* and fusion of the immunized B cells with a murine myeloma by standard methods. About 400 million hybridoma cells were screened for immunoactivity with HER3 in the presence and absence of heregulin, of which about 700 were positive for binding to both by initial ELISA assay and about 70 by FACS analysis for binding to intact cells. The screening employs the assays in the above cited U.S. Pat. No. 7,413,868.

Of these, six of these murine antibodies were assayed quantitatively for their binding affinities to HER3 ECD according to the commercially available FortéBio® method. In this method, ECD at 10-15 μg/ml was captured onto an amine-reactive surface in 10 mM MES, pH 6.0 at 25° C. Binding capacity is tested by treating the surface with unlabeled antibody. As unlabeled antibody accumulates on the surface, the optical characteristics of the surface are changed, thus allowing measurement of mass accumulation without requiring labeling. This is a modification of the Biacore™ style analysis. The antibodies were tested at 67 nM as the highest concentration and diluted in a three-fold dilution series. Response data for the various concentrations were individually and globally fitted to determine the binding affinities. The results for binding to HER3 ECD are summarized in Table 1

TABLE 1

Binding to HER3 ECD

|  | kD (pM) Average | Stdev |
|---|---|---|
| 14B10 | 18 | 4 |
| 1G4 | 2,810 | 2,660 |
| P1G1 | 115 | 89 |
| C27.1 | 281 | 168 |
| C31.1 | 349 | 185 |
| A28 | 2,140 | 2,500 |
| heregulin | 165,000 | 111,000 |

As shown, 14B10 showed the highest affinity but all of the six antibodies bound in the pM or nM range.

The binding assay was repeated for two of the antibodies, 1G4 and 14B10 using the same FortéBio® method. HER3 ECD at 10-15 μg/ml was again captured onto the amine surface in the same buffer. Heregulin at 10 μg/ml was added to form the HER3:heregulin complex on the surface and the antibodies once again tested at 67 nM using three-fold dilution series and the data were fitted to determine binding constants. These are listed in Table 2

TABLE 2

Binding to HER3-Heregulin Complex

|  | kD (pM) Average | Stdev |
|---|---|---|
| 1G4 | 327 | 113 |
| 14B10 | 34 | 15 |

Antibody 14B10 bound to HER3:heregulin complex at about the same affinity as to HER3. Antibody 1 G4 bound to HER3 alone with an affinity of 2.8 nM, but to the HER3:heregulin complex with an affinity of 327 pM. In both cases, the binding affinity for HER3 was tighter than that of heregulin itself which binds to HER3 ECD with an affinity of 165 nM.

Figure 1B:
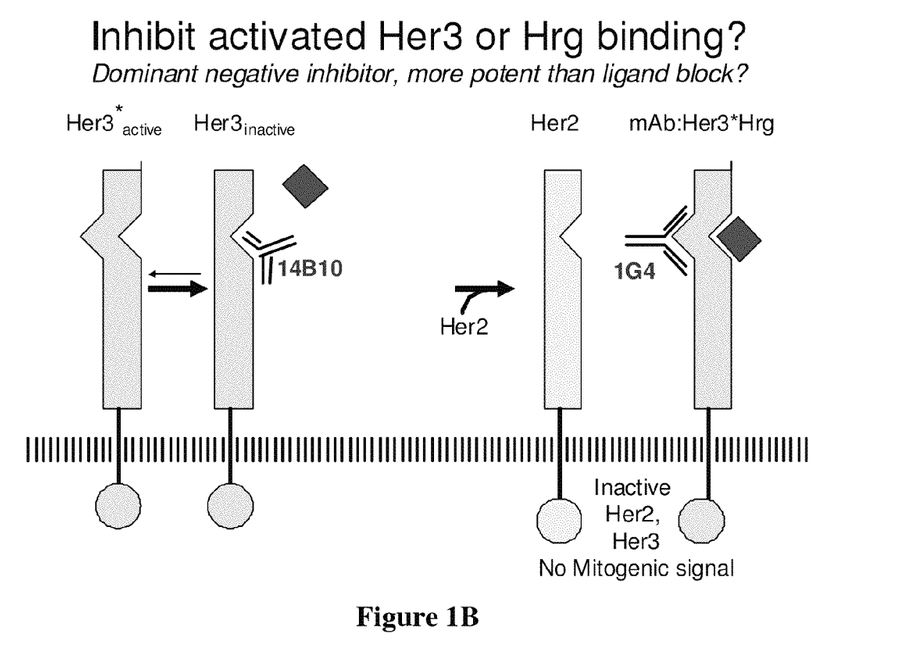

A diagram contrasting the apparent mode of action of these antibodies is shown in FIG. 1B.

Figure 2A:
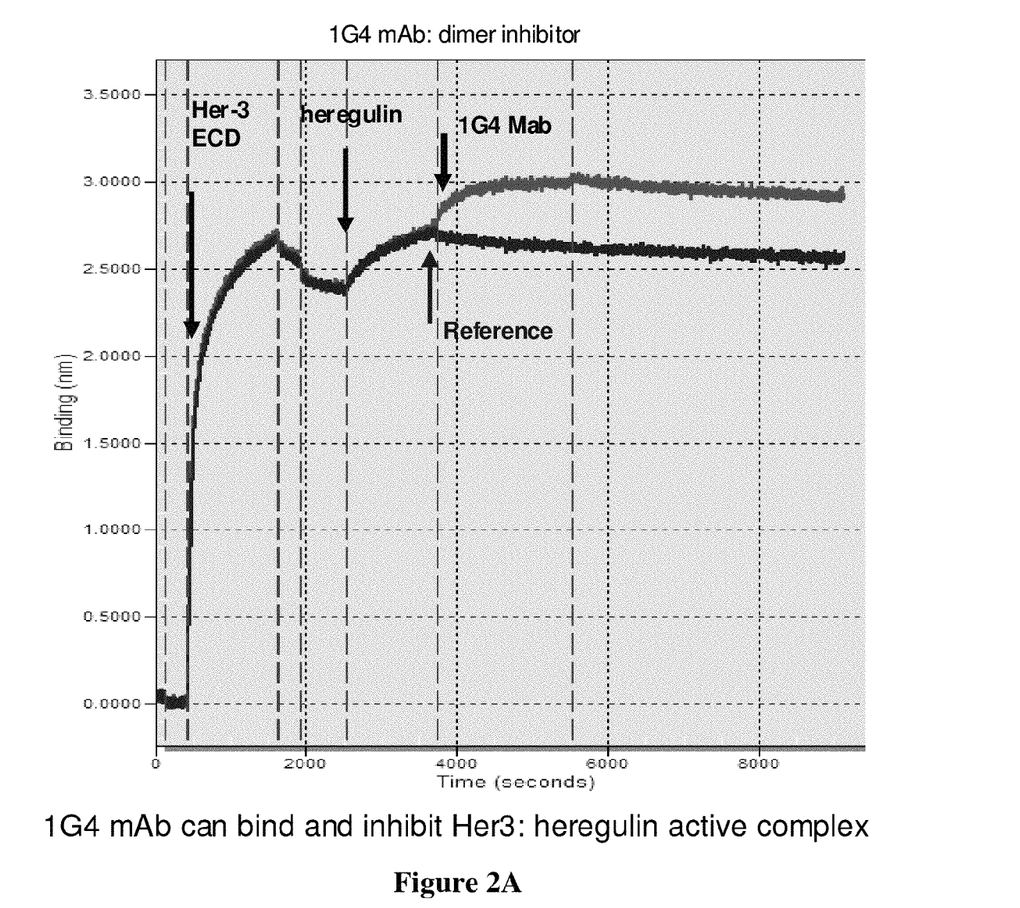
FIGS. 2A and 2B are graphs showing a comparison of binding of 1G4 mAb and 14B10 mAb to the heregulin active complex with HER3 as measured by FortéBio® biosensor.
Figure 2B:
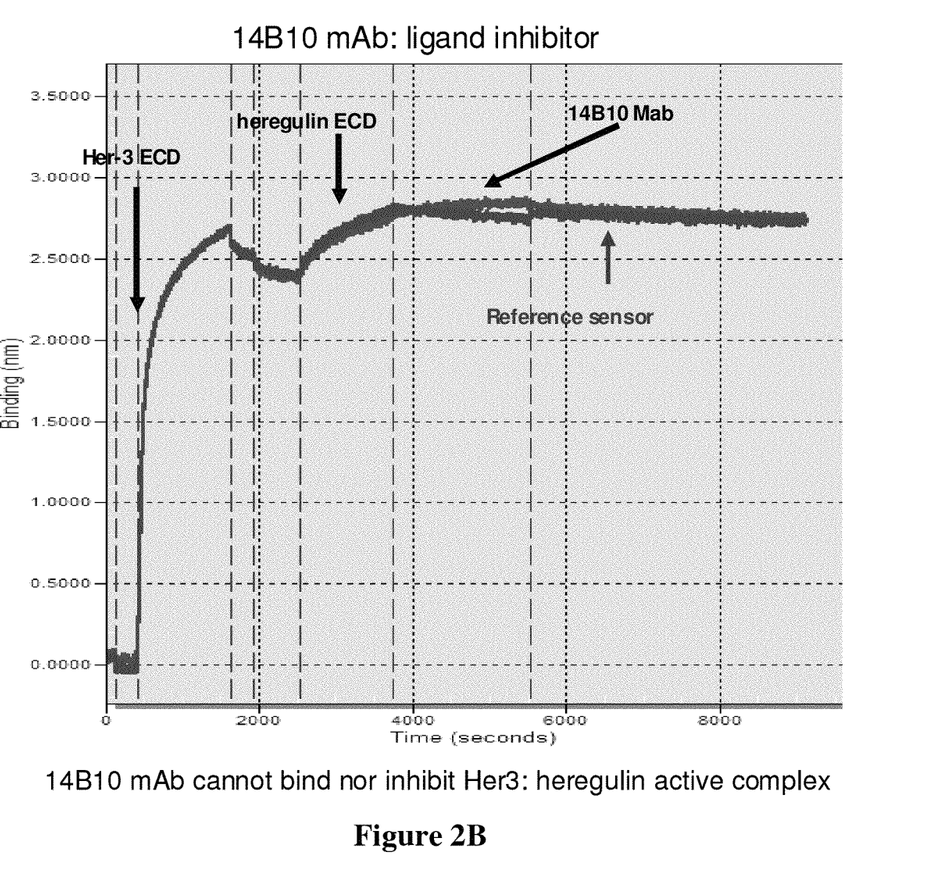

FIGS. 2A and 2B show a comparison between 1G4 and 14B10 in their ability to bind the complex of HER3 ECD with heregulin. As shown in FIG. 2A, 1G4 is able to bind the complex differentially, whereas 14B10 (FIG. 2B) does not.

Example 2

Effect on Tumor Cells

In addition, the ability of various antibodies to inhibit phosphorylation of tyrosine in HER3 and to inhibit cell growth in MCF-7 breast carcinoma cells cultured with heregulin was tested at various antibody concentrations.

To assess the ability of the antibodies to inhibit downstream phosphorylation, MCF-7 cells were maintained in log phase and for testing the medium was aspirated and the cells were rinsed, 2-3 ml of trypsin was added and the mixture incubated at 37° C. for 5 minutes. Trypsinization was stopped by adding 10-12 ml of growth medium and the cells were suspended for counting using a Becton Dickenson Vi-CELL™ cell counter and then plated at $10^4$ cells/well in 96-well plates at 100 μl/well. The plates were centrifuged at 960 rpm for 5 minutes and incubated at 37° C. for 4 hours, after which the medium was replaced with serum-free medium at 100 μl/well and the cells returned to the incubator for 3 days.

For the assay, purified antibodies at 1 μg/ml were added to each well and incubated at 37° C. for 1 hour, after which 20 nM heregulin 1b was added for 10 minutes to some of the wells. The media were aspirated from the cell surface and lysis buffer was added for determination of HER3 phosphorylation.

Figure 3A:
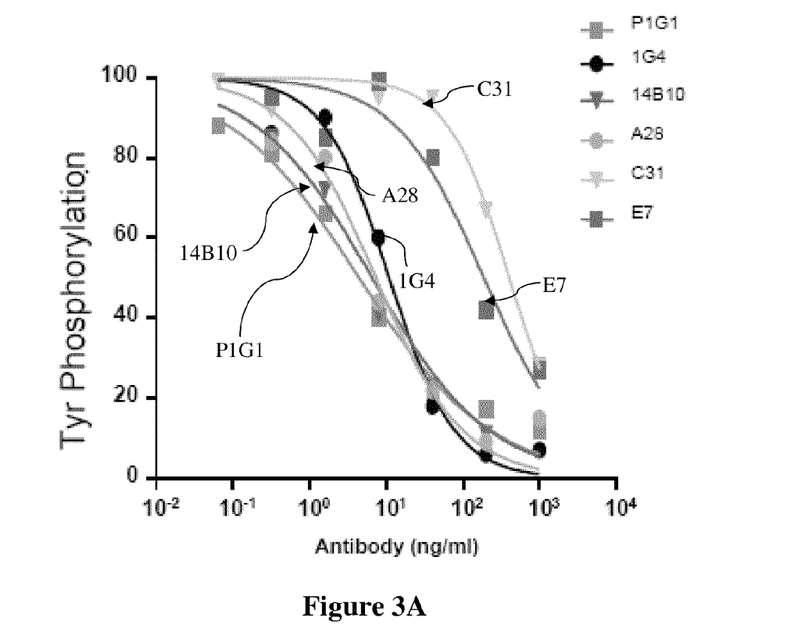
FIGS. 3A and 3B show the ability of various antibodies directed against HER3 to inhibit the growth of MCF-7 carcinoma cells and to inhibit tyrosine phosphorylation in these cells.

For this determination, a 96-well Greiner plate was coated with 2 μg/ml capture antibody in PBS at 100 μl/well and incubated at 4° C. overnight. The plate was then washed with PBST, blocked with 200 μl/well 3% BSA and PBS, washed twice with 300 μl PBST. Eighty μl of the cell lysate prepared in the previous paragraph was added to each well and incubated at room temperature with a rotator for 2 hours. The plate was then washed with PBST and then incubated with anti-phosphotyrosine labeled with horseradish peroxidase at 1:2000 for 2 hours. After washing, LumiGlo™ peroxidase solution KPL catalog number 54-61-00 was added at 100 μl/well and the extent of phosphorylation determined spectraphotometrically. The results are shown in FIG. 3A. As shown in these results, the $IC_{50}$ for 1G4 is about 10 ng/ml; whereas that for two other antibodies, E7 and C31, was much higher.

To assess effects on cell proliferation, MCF-7 cells were grown in flasks until confluent, then trypsinized and collected in growing media to stop trypsinization. The cells were then washed with starving media 3-4 times.

Figure 3B:
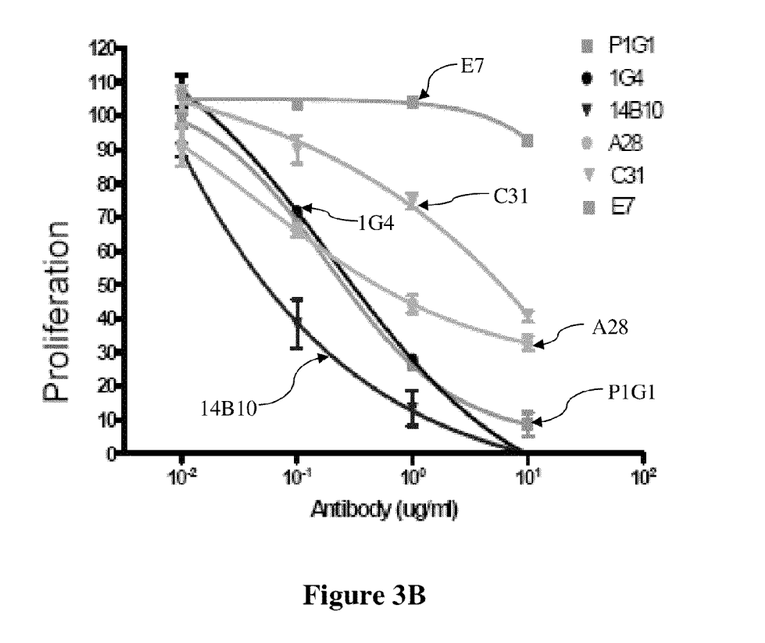

Sterile 96-well black clear-bottom plates were provided with 50 µl of starving media per well and incubated for 15 minutes at 37° C. The antibodies to be tested were diluted as desired in starving medium and seeded at 5,000 cells/50 µl into individual wells. The cells were incubated with antibody for 30 minutes at 37° C. and then 3 nM HRG added. The cells were then cultured for 5-6 days and cell proliferation measured by adding fluorescent dye Resazurin™ at 1:10 and incubated for 3 hours at 37° C. The plates were read on a fluorescent plate reader at 531/590 nm The results are shown in FIG. 3B.

As shown, 1G4 had an $EC_{50}$ between 0.1 µg/ml and 1 µg/ml; only 14B10 had a lower $EC_{50}$.

Figure 4:
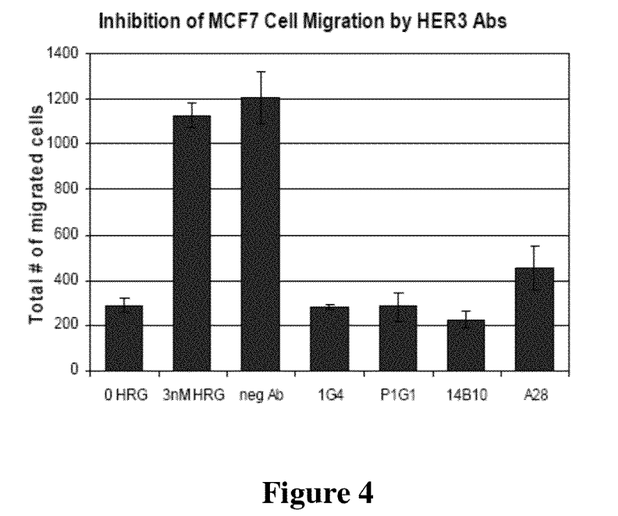
FIG. 4 shows the ability of various anti-HER3 antibodies to inhibit MCF-7 cell proliferation.

As shown in FIG. 4, several of the antibodies including 1 G4 were also able to block migration of cells stimulated with heregulin.

Figure 5:
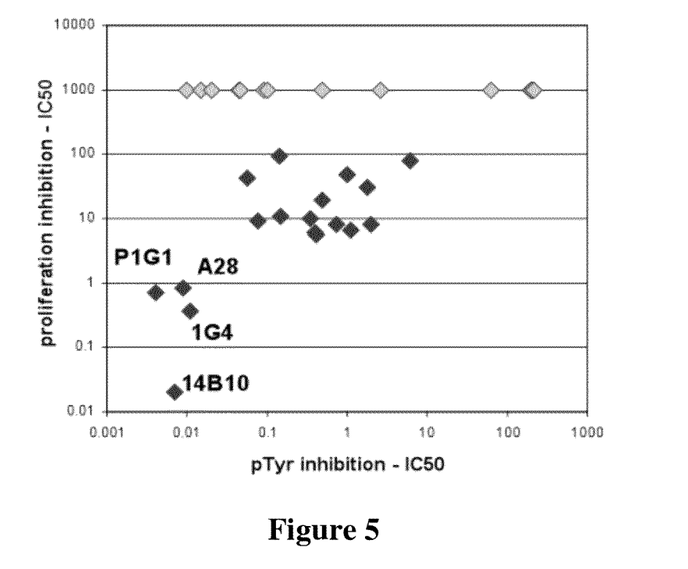
FIG. 5 shows that activity by the tyrosine phosphorylation measure of activity is not predictive of anti-proliferative activity.

It is important to note that inhibition of tyrosine phosphorylation does not guarantee or evaluate inhibition of proliferation, as shown in FIG. 5. Prior art teachings cited above have assumed that the two activities would be tightly correlated. By surveying 400 million hybridoma cells from seven libraries, a more comprehensive view of the activities was obtained, and lack of correlation established.

Example 3

Effect on Tumor Cells Expressing HER1

Figure 6:
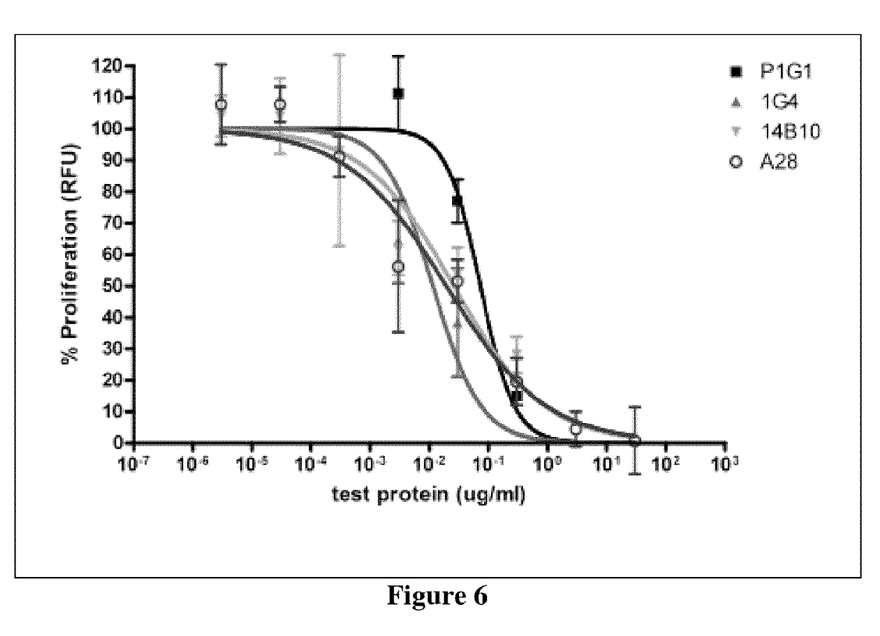
FIG. 6 shows the ability of various antibodies directed against HER3 to inhibit tyrosine proliferation in MB 468, a cell line that over-expresses HER1 and HER3 rather than HER2 and HER3.

The novel antibodies also inhibit tyrosine proliferation in a cell line that over-expresses HER1 and HER3, with no detectable HER2: MB468, human breast adenocarcinoma (Moasser, M. M., et al., *Cancer Res* (2001) 61:7184-7188). The cells were plated at 5,000 cells in 100 µl in DMEM/F12 50/50 plus 0.02% BSA-Transferrin. Under these conditions, titration of heregulin stimulation of proliferation established that 3 nM achieves 80% of the maximal stimulation. Antibody inhibition was thereby measureable along the linear dose/response part of the stimulation curve. The cells were cultured for 5 days and cell proliferation measured by adding fluorescent dye Resazurin™ as in the previous Example. The results are shown in FIG. 6. As shown, IG4, 14B10 and A28 have similar $EC_{50}$'s at approximately $10^{-3}$-$10^{-2}$ µg/ml. P1G1, however, has an $EC_{50}$ of about $10^{-1}$ µg/ml. Activity of the antibodies was then verified at 30 nM heregulin stimulation.

The invention claimed is:

1. A method to treat HER3-expressing cancer in a subject which method comprises administering to a subject in need of such treatment an effective amount of antibodies or fragments which bind to HER3 not complexed to heregulin, and which bind to HER3:heregulin complex with greater affinity as compared to binding uncomplexed HER3.

2. The method of claim 1 wherein the antibodies or fragments contain a heavy chain that comprises CDR1:GYTFTDYVIS (SEQ ID NO:4), CDR2:IYPGSGRY (SEQ ID NO:5) and CDR3:TRSLQRLRYFDV (SEQ ID NO:6).

3. The method of claim 2 wherein the antibodies or fragments further contain a light chain that comprises CDR1: RASQSISDYLH (SEQ ID NO:10), CDR2:YGSQSIS (SEQ ID NO:11) and CDR3:QQSNSWPLT (SEQ ID NO:12).

4. The method of claim 1 wherein the subject is human and said antibodies or fragments are human or humanized.

5. The method of claim 2 wherein the subject is human and said antibodies or fragments are human or humanized.

6. The method of claim 3 wherein the subject is human and said antibodies or fragments are human or humanized.

7. A method to treat HER3-expressing cancer in a subject which method comprises administering to a subject in need of such treatment an effective amount of a conjugate of a monoclonal antibody or fragment thereof which binds to HER3 not complexed to heregulin, and binds to HER3:heregulin complex with greater affinity as compared to binding uncomplexed HER3, said antibody or fragment coupled to a cytotoxic or chemotherapeutic agent.

8. The method of claim 7 wherein the antibody or fragment contains a heavy chain that comprises CDR1:GYTFTDYVIS (SEQ ID NO:4), CDR2:IYPGSGRY (SEQ ID NO:5) and CDR3:TRSLQRLRYFDV (SEQ ID NO:6).

9. The method of claim 8 wherein the antibody or fragment further contains a light chain that comprises CDR1:RASQ-SISDYLH (SEQ ID NO:10), CDR2:YGSQSIS (SEQ ID NO:11) and CDR3:QQSNSWPLT (SEQ ID NO:12).

10. The method of claim 7 wherein the subject is human and said antibody or fragment is human or humanized.

11. The method of claim 8 wherein the subject is human and said antibody or fragment is human or humanized.

12. The method of claim 9 wherein the subject is human and said antibody or fragment is human or humanized.

* * * * *